United States Patent [19]

Antranikian et al.

[11] Patent Number: 4,929,557
[45] Date of Patent: May 29, 1990

[54] THERMOSTABLE AMYLASES AND PULLULANASES FROM TWO ANAEROBIC MICROORGANISMS

[75] Inventors: Garabed Antranikian; Gerhard Gottschalk, both of Goettingen, Fed. Rep. of Germany

[73] Assignee: Kali-Chemie AG, Hanover, Fed. Rep. of Germany

[21] Appl. No.: 176,344

[22] Filed: Mar. 31, 1988

[30] Foreign Application Priority Data

Apr. 9, 1987 [DE] Fed. Rep. of Germany ........ 3712051

[51] Int. Cl.$^5$ ............................................. C12N 9/28
[52] U.S. Cl. .................................... 435/202; 435/201; 435/210; 435/252.1; 435/801; 435/822
[58] Field of Search ............ 435/201, 202, 210, 252.1, 435/801, 822

[56] References Cited

U.S. PATENT DOCUMENTS

| | | | |
|---|---|---|---|
| 4,572,898 | 2/1986 | Zeikus | 435/201 |
| 4,628,028 | 12/1986 | Katkocin et al. | 435/95 |

FOREIGN PATENT DOCUMENTS

| | | |
|---|---|---|
| 0131253 | 1/1985 | European Pat. Off. . |
| 0180952 | 5/1986 | European Pat. Off. . |
| 0184019 | 6/1986 | European Pat. Off. . |
| 0268193 | 5/1988 | European Pat. Off. . |
| 86/01831 | 3/1986 | World Int. Prop. O. . |
| 86/01832 | 3/1986 | World Int. Prop. O. . |

OTHER PUBLICATIONS

Plant et al., "Starch Degradation by Thermophilic Anaerobic Bacteria", Syst. Appl. Microbiol., vol. 9, Nos. 1-2, pp. 158-162 (1987), (CA 107: 20540g).
Koch et al., (Appl. Microbiol. Biotechnol., 27:192-198, 1987).
Hyun et al., *Applied & Environmental Microbiology,* 49:1168-1173, "General Biochemical Characterization of Thermostable . . . " (1985).

*Primary Examiner*—Robert A. Wax
*Attorney, Agent, or Firm*—Foley & Lardner, Schwartz, Jeffery, Schwaab, Mack, Blumenthal & Evans

[57] ABSTRACT

At least one type of excretable, thermostable amylolytic enzyme, such as amylase and pullulanase, can be recovered from a culture medium in which thermophilic anaerobic bacteria, such as *Thermoanaerobacter finii* or *Thermobacteroides acetoethylicus,* are propagated anaerobically in continuous culture, in the presence of a higher saccharide as carbon source, such an enzyme having a high stability at temperatures between 60° and 70° C. in absence of metal ions and substrate and under aerobic conditions.

27 Claims, 3 Drawing Sheets

4,929,557

THERMOSTABLE AMYLASES AND PULLULANASES FROM TWO ANAEROBIC MICROORGANISMS

BACKGROUND OF THE INVENTION

The present invention relates to excretable thermostable enzymes, namely, pullulanase and amylase, that are synthesized by and recoverable from thermophilic, anaerobic bacteria, such as *Thermoanaerobacter finii* and *Thermobacteroides acetoethylicus*.

The synthesis of amylolytic enzymes by thermophilic bacteria has been described. In the context of the present invention, amylolytic enzymes denote enzymes that break down starch and pullulan such as amylase and pullulanase respectively. According to published international patent application No. WO 86/01831, when *Clostridium thermohydrosulfuricum* ATCC 33,223 is cultured batchwise in a culture medium containing 0.5% soluble starch, the enzymes amylase, pullulanase and glucoamylase are formed, but these enzymes are retained intracellularly and are not released into the culture medium; compare also *Appl. Envir. Microbiol.* 49: 1168–1173 (1985).

According to published international patent application No. WO 86/01832, when *Clostridium thermosulfurogenes* ATCC 33,743 (same as DSM 2,229 deposited at Deutsche Sammlung von Mikroorganismen) is cultured batchwise in a culture medium with 0.5% soluble starch, the enzymes amylase and glucoamylase are formed, but only amylase is released into the culture medium.

To obtain amylase, pullulanase or both in any significant amounts from these bacteria, therefore, one has to propagate the bacteria, harvest and lyse them, and then separate the amylolytic enzymes from other cellular enzymes.

SUMMARY OF THE INVENTION

It is an object of the present invention, therefore, to provide a preparation comprising at least one type of excretable, thermostable, amylolytic enzyme that is produced in a process in which this enzyme is excreted in a significant amount into a culture medium by a species of thermophilic, anaerobic bacteria propagated in the medium.

It is also an object of the present invention to provide a preparation comprising at least one type of amylolytic enzyme that is thermostable, i.e., capable of maintaining high activity levels at a temperature higher than that normally tolerated by mesophilic bacteria, e.g., between about 60° C. and 90° C.

It is another object of the present invention to provide a preparation of at least one type of excretable, thermostable, amylolytic enzyme that can be easily recovered and harvested, without the necessity of lysing the bacterial cells that synthesize such enzymes.

It is also another object of the present invention to provide a preparation comprising at least one type of thermostable, amylolytic enzyme that is synthesized and excreted by thermophilic anaerobic bacteria that are capable of utilizing higher saccharides as a carbon source.

It is still another object of the present invention to provide a preparation comprising two types of excretable, thermostable, amylolytic enzymes, as described above.

It is yet another object of the present invention to provide a process for producing a preparation comprising at least one type of excretable, thermostable, amylolytic enzyme as described above.

In accomplishing these and other objects, there has been provided a preparation comprising at least one type of excretable, thermostable, amylolytic enzyme produced by a process comprised of the steps of (a) continuously culturing in a medium, under anaerobic conditions, a species of thermophilic anaerobic bacteria capable of excreting at least one type of amylolytic enzyme into the medium, and then (b) separating the bacteria from the medium, wherein said species of bacteria is selected from the group consisting of *Thermoanaerobacter finii* and *Thermobacteroides acetoethylicus*, and said medium comprises a nitrogen source, mineral salts and a carbon source that comprises an amount of a higher saccharide limiting to the growth of said bacteria.

In accordance with another aspect of the present invention, there has been provided a preparation as described above, wherein the extracellular enzyme is an amylase, a pullulanase or a combination of an amylase and a pullulanase.

In accordance with also another aspect of the present invention, there has been provided a substantially pure preparation of at least one type of excretable, thermostable, amylolytic enzyme produced in a process described below.

In accordance with still another aspect of the present invention, there has been provided a process for promoting the excretion of at least one type of excretable, thermostable, amylolytic enzyme comprising the steps of (a) continuously culturing in a medium, under anaerobic conditions, a species of thermophilic anaerobic bacteria capable of excreting at least one type of amylolytic enzyme into the medium, and then (b) separating the bacteria from the medium, wherein said species is selected from the group consisting of *Thermoanaerobacter finii* and *Thermobacteroides acetoethylicus*, and said medium comprises a nitrogen source, mineral salts and a carbon source that comprises an amount of a higher saccharide limiting to the growth of said bacteria.

In accordance with still another aspect of the present invention, there has been provided a process as described above, wherein said enzyme is an amylase or a pullulanase.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
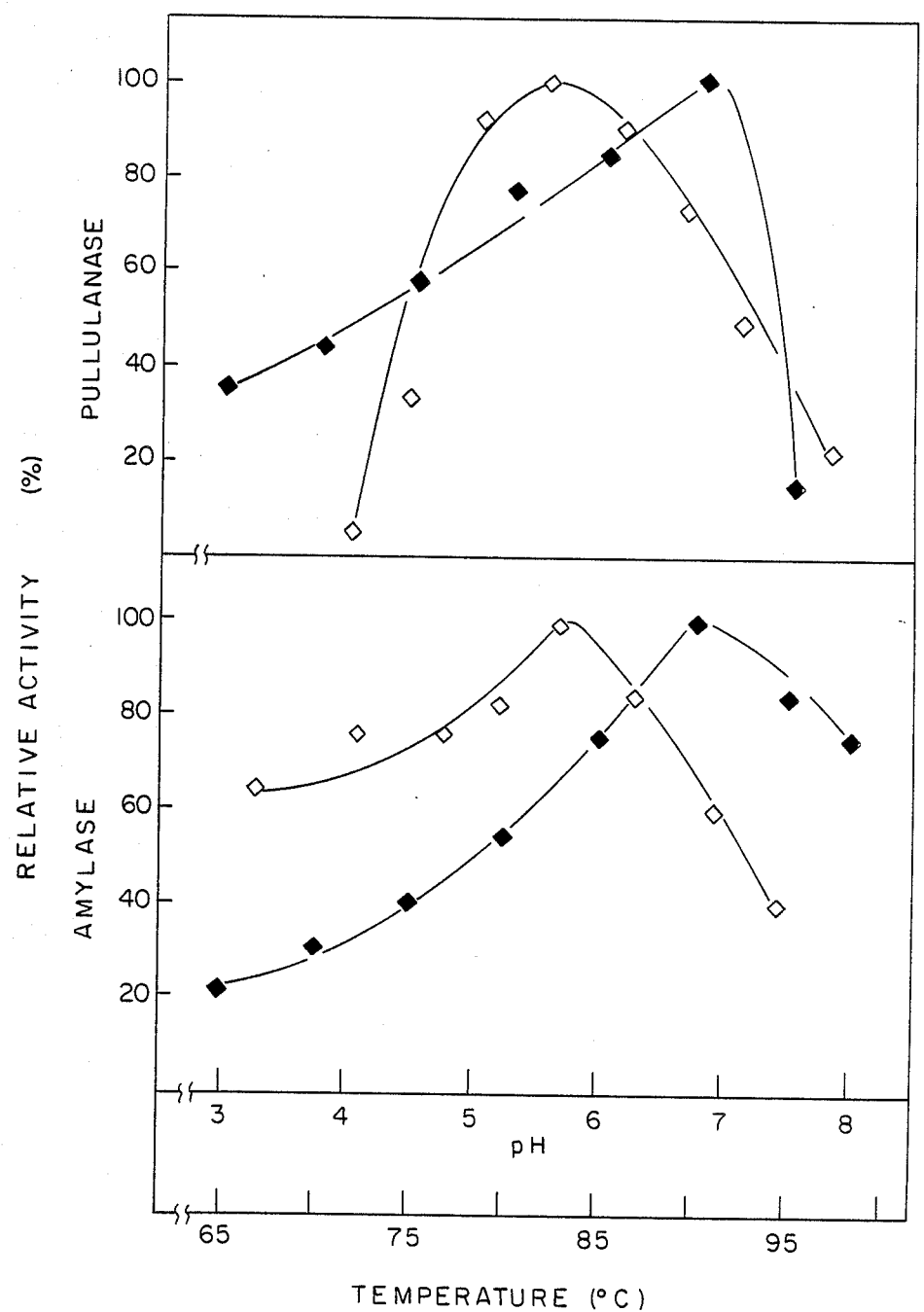
FIG. 1 shows the dependence of amylase and pullulanase activities, respectively, on pH and temperature, respectively, for *Thermoanaerobacter finii* DSM 3389.

It has been discovered that when thermophilic anaerobic bacteria, such as *Thermoanaerobacter finii* and *Thermobacteroides acetoethylicus,* are propagated anaerobically in a continuous culture in a medium comprising a higher saccharide, they can synthesize and excrete large amounts of thermostable amylolytic enzymes, such as amylase and pullulanase.

It has also been discovered that both amylase and pullulanase enzymes excreted by each of the species of bacteria mentioned above are optimally active in the same temperature and pH ranges so that both enzymes can be utilized together to hydrolyze starch.

It has further been discovered that both amylase and pullulanase enzymes excreted by each of the species of bacteria mentioned above (a) exhibit optimal activities at temperatures between 50° C. and 100° C., temperatures that are much higher than that normally tolerated by enzymes isolated from other, more common, mesophilic bacteria and (b) have a high stability at temperatures between 60° and 70° C. in absence of metal ions and substrate, and under aerobic conditions. Therefore, these thermostable amylase and pullulanase enzymes can be used in situations in which hydrolysis of starch at a high temperature is required.

Yet another discovery is that when starch is used as a substrate and carbon source, over 70% of the amylase and pullulanase synthesized by these bacteria are excreted into the culture medium in which these bacteria are propagated in continuous culture.

The culture medium within the context of the present invention further comprises a nitrogen source, mineral salts, and optionally vitamins and trace elements. In a preferred embodiment, the culture medium, in addition to a higher saccharide, further comprises the following constituents in % (weight/volume): amino acid/peptide mixture, produced by treating casein with trypticase, 0.25%; yeast extract, 0.1%; $KH_2PO_4$, 0.33%; $MgCl_2$, 0.016%; $CoCl_2.H_2O$, 0.0012%; cysteine-HCl, 0.05%. A suitable amino acid/peptide mixture is commercially available under the name Trypton. One ml each of a vitamin solution and a trace element solution may be added per liter of medium.

A "higher saccharide" in the context of the present invention is to be understood as excluding monsaccharides. Examples of higher saccharides are polysaccharides, such as starch, dextrin, or pullulan; oligosaccharides such as trisaccharides, for example, maltotriose, or disaccharides, for example, maltose; and mixtures thereof. The higher saccharide, when used as a carbon source, is present at a concentration that is limiting to the growth of the bacteria. "Limiting", as used herein, denotes a growth-determinative amount.

It is presumed to be within the ordinary skill of a person in the art to determine the suitable concentration of higher saccharide. For purposes of illustration only, it may be stated that the process can be carried out with a higher saccharide concentration of from about 0.1% to 3%, preferably about 0.2% to 1.5%, and particularly about 0.5% to 1.2% (weight/volume).

In the context of the present invention, a continuous culture refers to the propagation of bacterial cells in a culture medium such that, periodically, an amount of fresh culture medium is introduced into the culture vessel containing the bacterial cells, while an equal amount of cell-containing medium is removed from the vessel. Such a continuous culture may be carried out, for example, in a chemostat, an apparatus comprised of a culturing vessel and a supply vessel. In utilizing a chemostat, culture medium from a supply vessel is allowed to flow into the culturing vessel at a constant rate, and at the same time, bacterial suspension is allowed to exit from the culturing vessel at the same rate.

A continuous culture is generally carried out at a fixed "dilution rate" ("D"), wherein $D=f/V$, where f represents a flow rate in liters per hour and V represents a volume of medium in the culturing vessel. For example, a dilution rate of 0.036 per hour signifies that in the course of one hour, 36 ml of out of one liter of medium is replaced by fresh culture medium. Cell density in such a continuous culture may be controlled by limiting an amount of a nutrient, such as a carbon source, a nitrogen source or essential trace elements.

In contrast to a continuous culture, a batchwise culture as used in the context of the present invention denotes a culture condition in which no fresh medium is added to the culture vessel and no cells are removed prior to the harvest of all cells.

Other culture conditions within the context of the present invention includes a pH range of about 4 to 8, preferably about 5.0 to 7.5, and particularly about 5.5 to 7.0; a dilution rate of about 0.01 to 0.4, particularly about 0.02 to 0.3, preferably about 0.02 to 0.2 and most preferably about 0.03 to 0.15 per hour; and a temperature range of about 45° to 75° C., and preferably about 55° to 65° C.

The bacteria can be propagated in 2-liter or 5-liter fermentors with a culture volume of 1 to 2 liters. The cultures can be maintained in anaerobic condition by means of a continuous stream of nitrogen. The nitrogen can be sterilized, e.g., by passing it through a sterilized cotton filter. The cultures can be stirred at about 150 rpm. The pH-value can be measured with a glass electrode and can be adjusted by addition of 2N KOH.

Recovery and purification of these enzymes may be effected by any known laboratory techniques, and in particular, by a process described in the commonly owned, copending U.S. patent application, Ser. No. 121,136, filed Nov. 16, 1987, the contents of which are incorporated herein by reference.

The present invention is further described below by reference to the following examples.

EXAMPLE 1

Recovery of amylase and pullulanase, from respective batchwise or continuous culture of *Thermoanaerobacter finii* DSM 3389 and *Thermobacteroides acetoethylicus* DSM 2359

*T. finii* DSM 3389 and *T. acetoethylicus* DSM 2359 were propagated, respectively, in a batchwise culture or in a continuous culture in a medium comprising 1% (wt/vol) starch, at pH 6.5 and incubated at a temperature of about 65° C., under anaerobic conditions. When propagated in a continuous culture, *T. finii* DSM 3389 was cultured at a dilution rate of 0.036/hour and *T. acetoethylicus* DSM 2359 was cultured at a rate of 0.030/hour.

In propagating the bacteria, each of the above-mentioned strains of bacteria was inoculated into a fermentation vessel containing culture medium: one for batchwise culture and another for continuous culture. The vessels were then incubated for a certain period of time. When the bacterial cells in the continuous culture vessel entered a logarithmic growth phase, a continuous feed of fresh medium was supplied at a constant rate from a supply vessel to the culture vessel and an overflow valve was opened to keep the total volume in the culture vessel constant.

The amylolytic enzymes excreted into the culture medium were harvested by centrifugation of the cell suspension to separate the bacterial cells from the supernatant. Purification of these enzymes may be done in accordance with any known technique. The amounts of enzymes recovered under such culture conditions, expressed as units/liter (U/l), under such culture conditions are recorded in Table 1 below.

For both species of bacteria, it was found that not much amylolytic enzymes were synthesized when the bacteria were propagated in a batchwise culture; of the enzymes synthesized, more than 80% remained cell-bound. On the other hand, when these cells were propagated in a continuous culture, more amylolytic enzymes were synthesized and more than 70% of such enzymes were excreted into the culture medium.

TABLE 1

Recovery of the Amylase and Pullulanase from Batchwise and Continuous Culture of *Thermoanaerobacter finii* DSM 3389 and *Thermobacteroides acetoethylicus* DSM 2359.

| | Batchwise Culture | | Continuous Culture | |
|---|---|---|---|---|
| Organism | Amylase (U/l) | Pullulanase (U/l) | Amylase (U/l) | Pullulanase (U/l) |
| T. finii | 580 | 900 | 3000 | 3800 |
| T. acetoethylicus | 400 | 340 | 4100 | 3200 |

EXAMPLE 2

Activities of pullulanase and amylase recovered from a continuous culture of *Thermoanaerobacter finni*

*T. finii*, strain DSM 3389, was propagated in a continuous culture as described above. The enzymes pullulanase and amylase were recovered from the supernatant fluid in accordance with generally known laboratory techniques. The maximum amount of enzyme activity recovered from such a culture was as follows:

A. Pullulanase: 3800 U/l extracellular, more than 70% of the enzyme was in the supernatant.

B. Amylase: 3000 U/l extracellular, more than 70% of the enzyme was in the supernatant.

It was found that the conditions for optimum enzyme production in the continuous culture were:
pH 6.5
1% starch in the medium
dilution rate of 0.036/hour
temperature 65° C.

EXAMPLE 3

Activities of pullulanase and amylase recovered from a continuous culture of *Thermobacteroides acetoethylicus*

*T. acetoethylicus*, strain DSM 2359, was propagated in a continuous culture and the enzymes pullulanase and amylase were recovered as described above. The maximum amount of enzyme activity recovered from the supernatant was as follows:

A. Pullulanase: 3200 U/l extracellular, more than 70% of the enzyme was in the supernatant.

B. Amylase: 4100 U/l extracellular, more than 70% of the enzyme was in the supernatant.

The conditions of optimum enzyme production in the fermenter were found to be as follows:
pH 6.5
1% starch in the medium
throughput flow rate 0.030/hour
temperature 65° C.

EXAMPLE 4

Characteristics of amylase and pullulanase recovered from a continuous culture of *Thermoanaerobacter finii* DSM 3389

A. Determination of the optimum temperature for amylase- and pullulanase-activity.

Amylase and pullulanase enzymes were recovered from the supernatant fluid of a continuous culture of *T. finii*, as described above. These enzymes were purified in accordance with known laboratory techniques and their activities at various temperatures were assayed, again in accordance with established laboratory techniques.

In assaying for each enzyme activity, the enzyme was resuspended in a 20 mmol/l sodium acetate buffer at pH 5.5. The relative activity of these two enzymes as a function of temperature is represented by black diamonds in FIG. 1.

Both amylase and pullulanase were found to be optimally active at temperatures between about 50° C. and 95° C. As can be seen from FIG. 1, enzyme activities are optimal particularly between about 75° C. and 95° C., preferably between about 80° C. and 90° C., and especially preferably between about 85° C. and 90° C.

B. Determination of the optimum pH for amylase and pullulanase activity

A determination of the pH optimum for amylase and pullulanase activities, respectively, was carried out as above in a 20 mmol/l sodium acetate buffer at a temperature of about 90° C. As above, these enzymes were recovered from the supernatant fluid of a culture medium in which *T. finii* was propagated in a continuous culture. The relative activity of these two enzymes as a function of pH is represented by white diamonds in FIG. 1.

As can be seen from this Figure, both enzymes are optimally active between about pH 4.0 and 7.0, particularly between about pH 4.5 and 6.5, preferably between about pH 5.0 and 6.3 and especially between about 5.0 and 6.0.

Both amylase and pullulanase, therefore, are catalytically active under the same conditions of pH and temperature. Consequently, these enzymes can be used together to hydrolyze starch in a single stage. The studies above were carried out under aerobic conditions without addition of substrate or metal ions.

C. Determination of the influence of metal ions and cyclodextrins on amylase and pullulanase activity.

The influence of metal ions and cyclodextrins, respectively, on concentrated preparations of amylase and pullulanase, respectively, was studied. Each of the amylase or pullulanase recovered from *T. finii* DSM 3389 propagated in continuous culture was first dialyzed with respect to a 20 mM acetate buffer at pH 5.5. Each enzyme was then incubated in sodium phosphate buffer (20 mmol/l) at pH 5.5 with either metal ions, α-cyclodextrin or β-cyclodextrin, at a temperature of 90° C. Concentrations varying from between about 0 to 4 mmol of metal ions and from between about 0 to 10 mmol/l of α-cyclodextrin or β-cyclodextrin were used.

The activities of amylase and pullulanase as a result of the addition of metal ions or cyclodextrins are shown in Table 2 below. Results are expressed as percentages of the corresponding activity in the absence of metal ions or cyclodextrins. The values in each case represent the average value of 5 measurements.

(1Enzyme activity in the presence of metal ions.

The addition of up to 4 mmol/1 of metal ions including Mg, Ni, Mo and Co did not significantly affect enzyme activity. The addition of about 0.4 to 4.6 mmol/1 Ca ions, on the other hand, was found to increase pullulanase activity up to approximately 200%, but did not significantly affect amylase activity. The addition of other metal ions as shown in Table 2 produced intermediate effects on the enzyme activities.

(2) Enzyme activity in the presence of cyclodextrins.

In the presence of α-cyclodextrin (1 to 10 mmol/1), a slight decrease of both amylase and pullulanase activities was measured, though the decrease was not significant. For example, in the presence of 10 mmol/1 α-cyclodextrin, 70% of original enzyme activity could still be detected.

In the presence of β-cyclodextrin, a significant inhibition of pullulanase was observed. In contrast, little or no inhibition of amylase activity was observed.

TABLE 2

Influence of Divalent Cations and Cyclodextrins on the Activities of Amylase and Pullulanase from *T. finii* DSM 3389 and *T. acetoethylicus* DSM 2359.

| | T. finii | | T. acetoethylicus | |
|---|---|---|---|---|
| Conditions | Amylase (%) | Pullulanase (%) | Amylase (%) | Pullulanase (%) |
| No addition | 100 | 100 | 100 | 100 |
| Ca (mmol/l) | | | | |
| 0.4 | 85 | 210 | 130 | 100 |
| 1.6 | 90 | 200 | 40 | 90 |
| 4.6 | 120 | 190 | 20 | 90 |
| Zn (mmol/l) | | | | |
| 0.4 | 75 | 75 | 85 | 95 |
| 1.6 | 40 | 50 | 70 | 60 |
| 4.0 | 0 | 25 | 10 | 10 |
| Cu (mmol/l) | | | | |
| 0.4 | 95 | 90 | 100 | 100 |
| 1.6 | 0 | 30 | 40 | 45 |
| 4.0 | 0 | 0 | 5 | 10 |
| Mn (mmol/l) | | | | |
| 0.4 | 85 | 130 | 105 | 125 |
| 1.6 | 100 | 115 | 95 | 65 |
| 4.0 | 140 | 95 | 85 | 60 |
| EDTA (mmol/l) | 50 | 20 | 35 | 45 |
| beta-cyclodextrin (mmol/l) | | | | |
| 1 | 105 | 15 | 60 | 20 |
| 2 | 105 | 5 | 45 | 10 |
| 5 | 95 | 5 | 40 | 10 |
| 7.5 | 100 | 5 | 50 | 5 |
| 10 | 100 | 0 | 40 | 0 |

D. Temperature stability of the enzymes.

Extracellular pullulanase and amylase, respectively, recovered from the supernatant fluid of a continuous culture of *T. finii* were sterilized by filtration and incubated at about 60° C., 65° C., 70° C. and 80° C, respectively, under aerobic conditions at pH 5.5 in the absence of metal ions or substrate. Activities of these enzymes were assayed after a certain period of incubation.

Results showed that no substantial loss of amylase or pullulanase activities, respectively, occurred after 80 hours at 60° C. and 65° C. The enzyme activities measured under the same conditions at 65° C., 70° C. and 80° C. are shown in FIG. 3.

Figure 3:
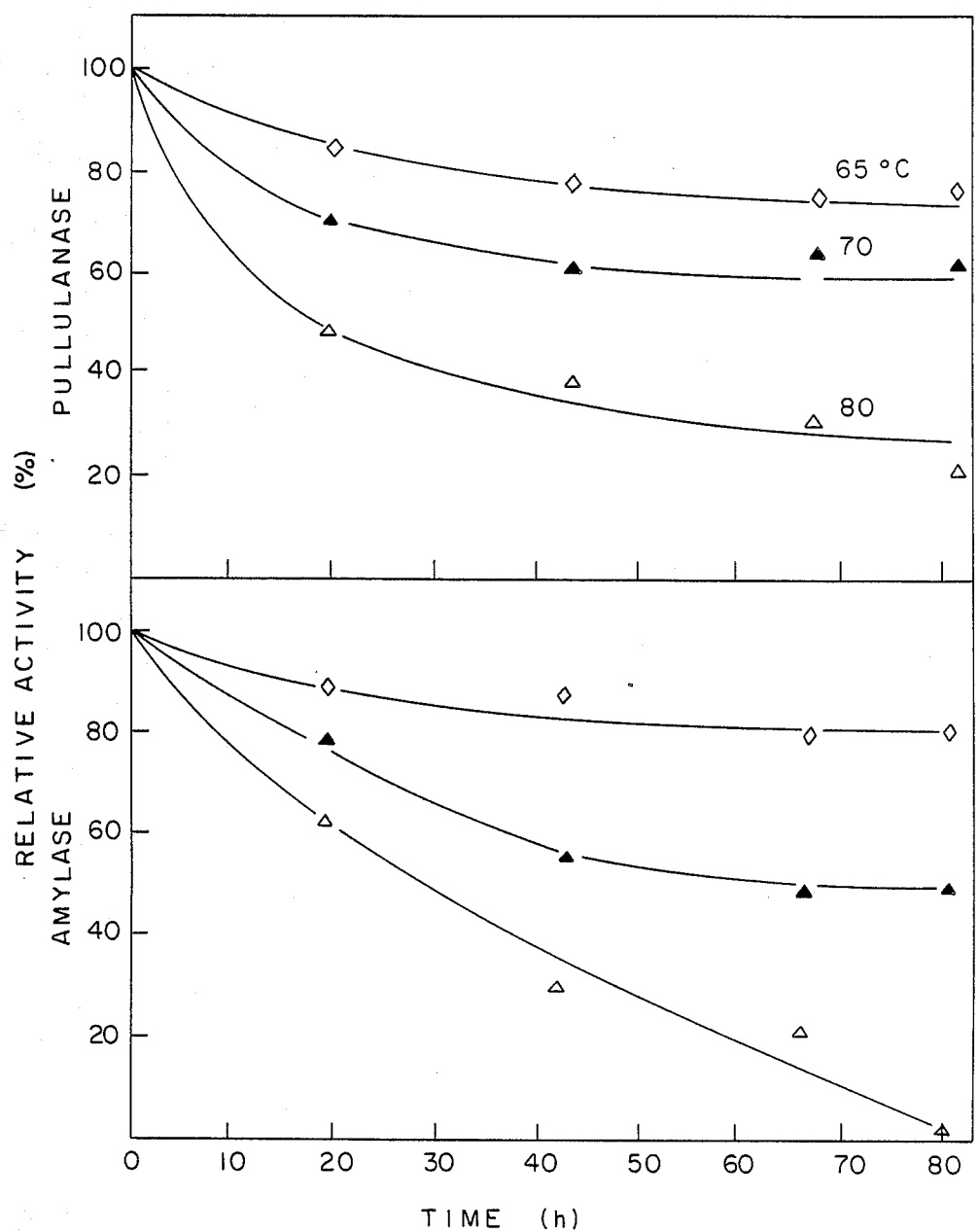
FIG. 3 shows the dependence of the amylase and pullulanase activities, respectively, on the duration of time these enzymes from *Thermoanaerobacter finii* DSM 3389 were held at temperatures between 60° C. and 80° C.

More specifically, FIG. 3 shows that the amylase activity is approximately 90% of its starting value after about 40 hours of incubation at about 65° C. and approximately 80% of its starting value after about 80 hours at about 65° C. At about 70° C., amylase loses approximately 20% of its starting activity after about 20 hours, approximately 45% after about 42 hours and approximately 50% after about 80 hours. At 80° C., the corresponding loss in amylase activity is approximately 35% after 20 hours and approximately 100% after 80 hours.

FIG. 3 further shows the stability of pullulanase activity at temperatures of about 65° C., 70° C. and 80° C. As can be seen from this Figure, pullulanase activity is approximately 85% of its starting value after 20 hours, and approximately 80% after about 80 hours at 65° C. At 70° C., pullulanase loses approximately 30% of its starting activity after about 20 hours and approximately 35% after 80 hours. At 80° C., the corresponding loss in pullulanase activity is approximately 50% after 20 hours and approximately 70% after about 80 hours.

EXAMPLE 5

Characteristics of amylase and pullulanase recovered from a continuous culture of *Thermobacteroides acetoethylicus* DSM 2359

A. Determination of the optimum temperature for amylase and pullulanase activity.

Figure 2:
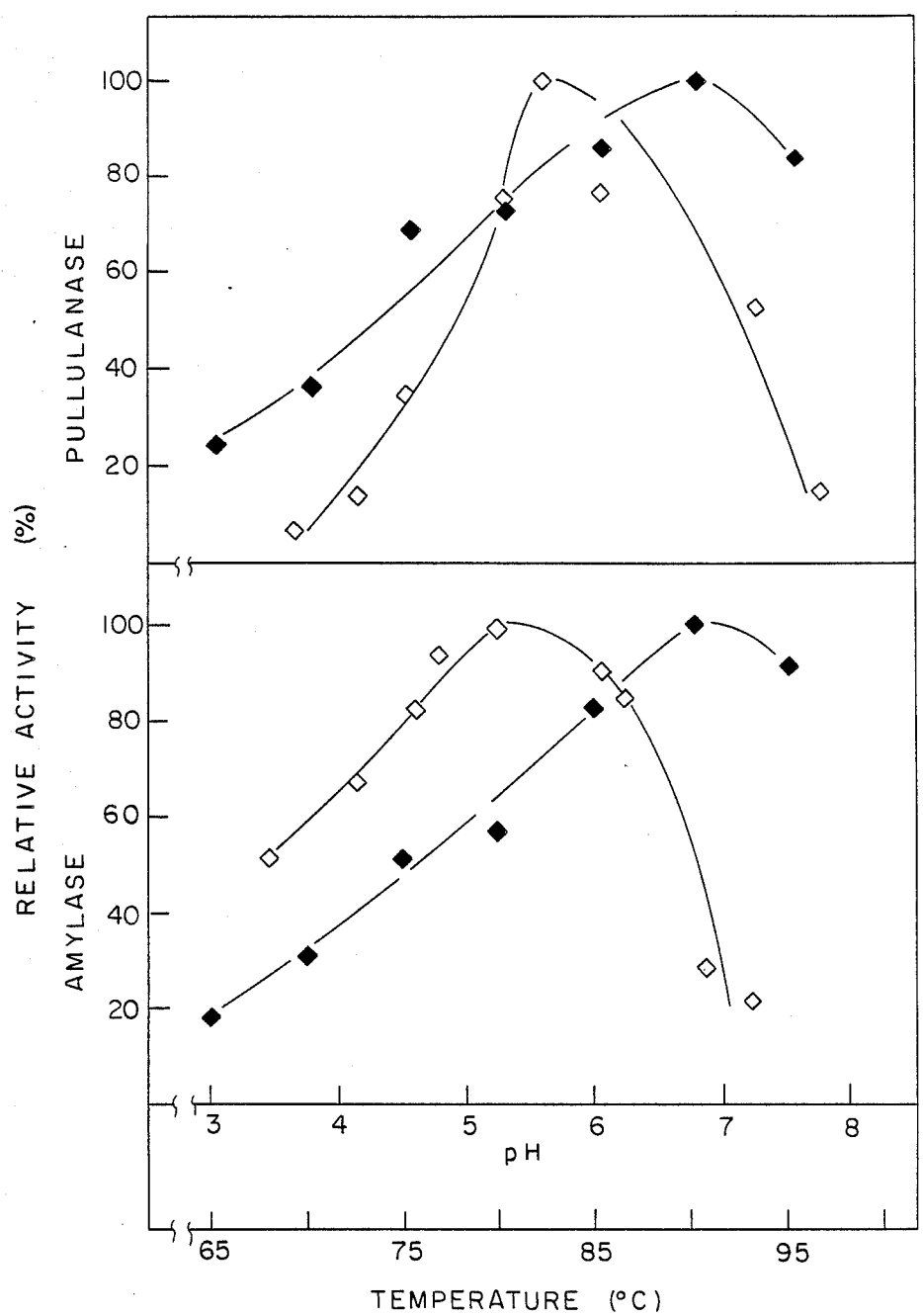
FIG. 2 shows the dependence of the amylase and pullulanase activities, respectively, on pH and temperature, respectively, for *Thermobacteroides acetoethylicus* DSM 2359.

A determination of the optimum temperature for amylase and pullulanase activities, respectively, was performed as in Example 4 above. The enzymes were recovered from the supernatant fluid of a culture medium in which *T. acetoethylicus* was propagated in continuous culture. The relative activities of these two enzymes as a function of temperature are represented by black diamonds in FIG. 2.

As can be seen from this Figure, both enzymes are optimally active at temperatures between about 65° C. and 100° C., particularly between about 75° C. and 100° C., preferably between about 80° C. and 95° C., and especially preferably between about 85° C. and 95° C.

B. Determination of the optimum pH for amylase and pullulanase activity.

A determination of the pH optimum for amylase and pullulanase activities, respectively, was performed as in Example 4 above. These enzymes were recovered from supernatant fluid of culture medium in which *T. acetoethylicus* was propagated. The relative activities of these two enzymes as a function of pH are represented by white diamonds in FIG. 2.

As can be seen from this Figure, both enzymes are optimally active between about pH 4.0 and 7.0, particularly between about 4.5 and 6.5 and preferably between about 5.0 and 6.0.

Both amylase and pullulanase, therefore, are catalytically active under the same conditions of pH and temperature. Accordingly, the two enzymes can be used together to hydrolyze starch in a single step. The studies above were carried out under aerobic conditions and without addition of substrate or metal ions.

C. Determination of the influence of metal ions and cyclodextrins on amylase and pullulanase activity.

The influence of metal ions and cyclodextrins, respectively, on concentrated preparations of amylase and pullulanase, respectively, was measured as in Example 4 above. Each of the amylase or pullulanase recovered from *T. acetoehtylicus* propagated in continuous culture was first dialyzed with respect to a 20 mM acetate buffer at pH 5.5. Results are tabulated in Table 2 above.

(1) Enzyme activity in the presence of metal ions.

As can be seen from Table 2, presence of Ca ions did not stimulate either pullulanase or amylase activity. The addition of up to 4 mmol/l of metal ions including Mg, Ni, Mo and Co did not significantly affect the enzyme activities. The addition of other metal ions, as shown in Table 2, produced intermediate effects on the enzyme activities.

(2) Enzyme activity in the presence of cyclodextrins

As in Example 4 above, in the presence of α-cylodextrin (1 to 10 mmol/l), a slight decrease of both amylase and pullulanase activities was measured, though the decrease was not significant. For example, in the presence of 10 mmol/l of α-cylodextrin, 70% of original enzyme activities could still be detected. β-cyclodextrin inhibited the activity of amylase slightly, but inhibited the activity of pullulanase substantially.

D. Temperature stability of the enzymes.

Extracellular pullulanase and amylase, respectively, recovered from the supernatant fluid of a continuous culture of *T. acetoethylicus* were sterilized by filtration and incubated as above. Activities of these enzymes were assayed after a certain period of incubation.

No loss of enzyme activity was observed after 80 hours at about 60° C. at pH 5.5 under aerobic conditions in the absence of substrate and without addition of metal ions. After 80 hours at 70° C., 60% of the amylase and pullulanase activities, respectively, were observed.

What is claimed is:

1. A preparation comprising at least one type of excretable, thermostable, amylolytic enzyme produced by a process comprised of the steps of (a) continuously culturing in a medium, under anaerobic conditions, a species of thermophilic anaerobic bacteria capable of excreting at least one type of amylolytic enzyme into the medium, and then (b) separating the bacteria from the medium, wherein said species of bacteria is selected from the group consisting of *Thermoanaerobacter finii* and *Thermobacteroides acetoethylicus,* and said medium comprises a nitrogen source, mineral salts and a carbon source that comprises an amount of a higher saccharide limiting to the growth of said bacteria.

2. A preparation according to claim 1, wherein said amylolytic enzyme is an extracellular enzyme.

3. A preparation according to claim 1, wherein said species of bacteria is a *Thermoanaerobacter finii* species.

4. A preparation according to claim 3, wherein said species of bacteria is a *Thermoanaerobacter finii,* strain DSM 3389.

5. A preparation according to claim 3, wherein said enzyme is an amylase.

6. A preparation according to claim 5, wherein said amylase is optimally active between about 85° C. and 90° C., and between about pH 5.0 and 6.0, and wherein the activity of said amylase enzyme is stable at about 60° C. under aerobic conditions in the absence of substrate and metal ions.

7. A preparation according to claim 3, wherein said enzyme is a pullulanase.

8. A preparation according to claim 7, wherein said pullulanase is optimally active between about 85° C. and 90° C., and between about pH 5.0 and 6.0, and wherein the activity of said pullulanase is enhanced by the presence of calcium ions and inhibited by β-cyclodextrin, and is stable at 60° C. under aerobic conditions in the absence of substrate or metal ions.

9. A preparation according to claim 1, wherein said species of bacteria is a *Thermobacteroides acetoethylicus* species.

10. A preparation according to claim 9, wherein said species of bacteria is a *Thermobacteroides acetoethylicus,* strain DSM 2359.

11. A preparation according to claim 9, wherein said enzyme is an amylase.

12. A preparation according to claim 11, wherein said amylase is optimally active between about 85° C. and 95° C., and between about pH 5.0 and 6.0; and wherein activity of said amylase is slightly inhibited by presence of β-cyclodextrin and is stable at about 60° C. under aerobic conditions in the absence of substrate and metal ions.

13. A preparation according to claim 9, wherein said enzyme is a pullulanase.

14. A preparation according to claim 13, wherein said pullulanase is optimally active between about 85° C. and 95° C., and between about pH 5.0 and 6.0; and wherein the activity of said pullulanase is inhibited by presence of β-cyclodextrin and is stable at about 60° C. under aerobic conditions in the absence of substrate and metal ions.

15. A preparation according to claim 1, wherein said preparation comprises two types of excretable, thermostable, amylolytic enzymes.

16. A preparation according to claim 15, wherein said two types of enzymes are amylase and pullulanase.

17. A substantially pure preparation comprising at least one type of excretable, thermostable, amylolytic enzyme produced by a process comprised of the steps of (a) continuously culturing in a medium, under anaerobic conditions, a species of thermophilic anaerobic bacteria capable of excreting at least one type of amylolytic enzyme into the medium, and then (b) separating the bacteria from the medium, wherein said species is selected from the group consisting of *Thermoanaerobacter finii* and *Thermobacteroides acetoethylicus,* and said medium comprises a nitrogen source, mineral salts and a carbon source that comprises an amount of a higher saccharide limiting to the growth of said bacteria.

18. A substantially pure preparation according to claim 17, wherein said amylolytic enzyme is an amylase or a pullulanase.

19. A process for promoting the excretion of at least one type of thermostable amylolytic enzyme comprising the steps of (a) continuously culturing in a medium, under anaerobic conditions, a species of thermophilic anaerobic bacteria capable of excreting at least one type of amylolytic enzyme into the medium, and then (b) separating the bacteria from the medium, wherein said species of bacteria is selected from the group consisting of *Thermoanaerobacter finii* and *Thermobacteroides acetoethylicus,* and said medium comprises a nitrogen source, mineral salts and a carbon source that comprises an amount of a higher saccharide limiting to the growth of said bacteria.

20. A process according to claim 19, wherein said continuous culture is carried out at a temperature of about 65° C.

21. A process according to claim 19, wherein the pH of said medium is about 6.5.

22. A process according to claim 19, wherein said continuous culture is carried out at a dilution rate of about 0.030 to 0.036 per hour.

23. A process according to claim 19, wherein said carbon source is starch.

24. A process according to claim 19, wherein said amount of higher saccharide is 1% (wt/vol).

25. A process according to claim 19, wherein said amylolytic enzyme is an amylase or a pullulanase.

26. A process according to claim 19, wherein said process promotes the excretion of two types of excretable, thermostable, amylolytic enzymes.

27. A process according to claim 26, wherein said two types of enzyme are amylase and pullulanase.

* * * * *